United States Patent [19]

Hoffmann et al.

[11] 4,058,623

[45] Nov. 15, 1977

[54] PROSTAGLANDIN-CONTAINING LYOPHILIZED POWDERS

[75] Inventors: Rolf-Rüdiger Hoffmann; Peter Fuchs, both of Berlin, Germany

[73] Assignee: Schering Aktiengesellschaft, Berlin and Bergkamen, Germany

[21] Appl. No.: 669,336

[22] Filed: Mar. 22, 1976

[30] Foreign Application Priority Data

Apr. 4, 1975 Germany .............................. 2515001

[51] Int. Cl.$^2$ .................... A61K 31/19; A61K 31/215
[52] U.S. Cl. ..................................... 424/317; 424/305
[58] Field of Search ................................ 424/305, 317

[56] References Cited

U.S. PATENT DOCUMENTS

| 3,904,679 | 9/1975 | Bandy | 424/317 |
|---|---|---|---|
| 3,954,787 | 5/1976 | Monkhouse | 424/317 |

*Primary Examiner*—Sam Rosen
*Attorney, Agent, or Firm*—Millen & White

[57] ABSTRACT

Lyophilized prostaglandin-containing powders are stabilized with tris(hydroxymethyl)-aminomethane hydrochloride.

19 Claims, No Drawings

PROSTAGLANDIN-CONTAINING LYOPHILIZED POWDERS

BACKGROUND OF THE INVENTION

This invention relates to prostaglandin-containing lyophilized powders and use thereof to produce aqueous solutions or solid pharmaceutical preparations for enteral, parenteral, and topical application and to processes of preparing prostaglandin-containing lyophilized powders.

Prostaglandins are hydroxy-fatty acids derived from prostanoic acid:

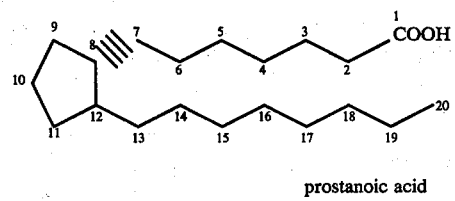

prostanoic acid

Prostaglandins include both naturally-occurring prostaglandins and synthetic analogs of natural prostaglandins.

Natural prostaglandins include, for example, prostaglandins $A_1$, $A_2$, $E_1$, $E_2$, $E_3$, $F_{1\alpha}$, $F_{2\alpha}$, $B_1$, $B_2$, $D_1$, and $D_2$. $PGE_2$ has a cis-5,6-double bond, a trans-13,14-double bond, a C-9-keto group, and an α-hydroxy group at the 11- and 15-positions of prostanoic acid.

Exemplary of synthetic analogs of natural prostaglandins are $C_1$-carboxylic acid esters and amides, 19-oxa-, 17-substituted-ω-tris-nor-, and 16-substituted-ω-tetra-nor- prostaglandins. Hydroxy groups in the 9-, 11- and/or 15-position can be etherified or esterified, or a 15-hydroxy group can be oxidized to the keto group and be ketalized. Double bonds in the 10,11- or 13,14-position can collectively be substituted by a methylene or hydrogenated.

Prostaglandins are of great interest owing to their remarkable biological and pharmacological characteristics. However, prostaglandins, especially prostaglandin E derivatives, are relatively unstable. Attempts to stabilize prostaglandins using a suitable carrier material have generally been unsuccessful.

Methanolic solutions of prostaglandins $PGE_1$ and $PGE_2$ are stable depending on pH, for up to 40 days at room temperature, Eur. J. Pharmacol. 4 (1968) 416–420. However, methanolic solutions are toxic and cannot be employed in medicine.

Solutions of $PGE_2$ in absolute ethanol can be preserved for at least 6 months at −20° C., Amer. J. Hosp. 30 (1973) 236–239. Ethanolic solutions are unsuitable for medical use without dilution by water or other carrier materials prior to use. Moreover, $PGE_2$ in ethanol at 4° C. loses 5–12% of its activity within a month and $PGE_2$ decomposes so rapidly in NaCl solution that only 58–62% of the original activity remains after 15 days. Lipids 8, 10 (1973) 592–594.

In U.S. Pat. No. 3,826,823 are described prostaglandin preparations stabilized with polyvinylpyrrolidone. In a preferred embodiment, a prostaglandin material and polyvinylpyrrolidone are dissolved in methylene dichloride and concentrated by evaporation under vacuum at 50° C. The dry powder obtained from the film, or pharmaceutical preparations made therefrom, can be preserved for 8 months at room temperature. Since 10–1000 parts of polyvinylpyrrolidone are used per 1 part of prostaglandin, the prostaglandin material to be formulated is already present at a very high dilution. Therefore, it is impossible to obtain highly concentrated prostaglandin preparations by this process.

Pharriss, in U.S. Pat. No. 3,882,241, discloses a variety of stabilizing and/or suspending agents for prostaglandins, including polyvinylpyrrolidone.

Monkhouse, U.S. Pat. No. 3,851,052, describes polyvinylpyrrolidone as a binding agent with prostaglandins stabilized by an alkali metal sulfite salt.

Andersen et al., in U.S. Pat. No. 3,723,423, and Zaffaroni, in U.S. Pat. No. 3,845,111, suggest that sorbitan monolaurate, triethanolamine oleate, polyoxyethylene sorbitan monopalmityl or dioctyl sodium sulfosuccinate are emulsifiers, preservatives and/or wetting agents for formulations of prostaglandin ethers.

Bergstrom, U.S. Pat. No. 3,598,858, notes the use of gelatin, lactose, starches, magnesium stearates, plus auxiliary substances, including preservatives, in prostaglandin formulations.

Therefore, there is a continuing need for prostaglandin-containing lyophilized powders which are stable over a long period of time and suitable for the preparation of aqueous solutions and solid galenic preparations.

This problem is solved by freeze-drying prostaglandin material contained in an aqueous solution containing tris (hydroxymethyl) aminomethane hydrochloride and optionally an inert filler. Thus, addition of tris (hydroxymethyl) aminomethane hydrochloride to prostaglandin material effects a substantial improvement in the stability thereof.

Surprisingly, addition of tris (hydroxymethyl) aminomethane hydrochloride considerably improves stability of prostaglandin $E_2$ to lyophilization and subsequent storage.

SUMMARY OF THE INVENTION

In a compositional aspect, this invention relates to a storage-stable lyophilized prostaglandin composition comprising a prostaglandin compound and a decomposition-inhibiting quantity of tris (hydroxymethyl) aminomethane hydrochloride or other acid-addition salt thereof.

In a process aspect, this invention relates to a process for preparing a storage-stable lyophilized prostaglandin composition, comprising dissolving a prostaglandin compound and tris (hydroxymethyl) aminomethane in a solvent, bringing the pH of the solution to 5–7 by introduction of an acid, filtering said solution, and lyophilizing the filtrate from said solution.

In another compositional aspect, this invention relates to an aqueous solution of a prostaglandin compound and decomposition-inhibiting quantity of an acid addition salt of tris (hydroxymethyl) aminomethane, said solution having a pH of about 5–7.

This invention further relates to the use of aforesaid lyophilized compositions for the production of preparations for enteral, parenteral or topical administration in human or veterinary medicine.

DETAILED DESCRIPTION

Since prostaglandins are very potent substances, only very small amounts of prostaglandins are usually administered. Therefore, it has been the practice to add during a lyophilization procedure inert fillers, including but not limited to, polyvinylpyrrolidone, sorbitol, mannitol, lactose, cyclodextrins, glycine. These materials are normally introduced during lyophilization in order to obtain a preparation having a fine, highly porous structure imparting to the lyophilized product a high rate of dissolution in water or physiological NaCl solution, for example, in making preparations for intravenous injection. In the present invention polyvinylpyrrolidone is preferably used as filler.

Suitable solvents for lyophilization are water or mixtures of water and water-miscible, highly-volatile solvents, including, but not limited to, ethanol, acetone, and dioxane.

The invention accordingly relates to lyophilized prostaglandin-containing powders, containing tris(hydroxymethyl)-aminomethane hydrochloride and, optionally, an inert filler.

To prepare the lyophilized powder of this invention, the prostaglandin compound or compounds is dissolved with the addition of tris(hydroxymethyl) aminomethane and, optionally, a filler, and the solution is brought to pH 5–7 by addition of hydrogen chloride. After filtration, the solution is freezedried.

The lyophilized powder can also be made by dissolving the prostaglandin compound, another tris(hydroxymethyl) aminomethane acid addition salt and, optionally, a soluble inert filler in water and further processing as above.

The ratio of prostaglandin to tris(hydroxymethyl)-aminomethane hydrochloride and filler can be varied over wide ranges. Since some prostaglandins are more stable than others, the amount of the tris(hydroxymethyl)aminomethane hydrochloride added thereto also depends on the stability of the prostaglandins. In case of relatively unstable prostaglandins, such as PGEs and their synthetic analogs and derivatives, larger amounts of tris(hydroxymethyl)aminomethane hydrochloride are utilized, and lesser quantities are employed for relatively stable prostaglandins, e.g., $PGF_{2\alpha}$ and its synthetic analogs and derivatives. The proportion also depends, inter alia, on the concentration of prostaglandin required in the dosage form ultimately administered.

For example, it is possible to add 1–1000, preferably 1–200 parts of tris(hydroxymethyl)aminomethane hydrochloride, and 0–1000, preferably 1–200 parts, of a filler per part of prostaglandin. In the foregoing, parts are by weight.

With the relatively unstable prostaglandins, it is preferred to use 1–1000 parts by weight of tris(hydroxymethyl)aminomethane hydrochloride, most preferably 1–200 parts, per part of prostaglandin compound. In the case of relatively stable prostaglandin compounds, preferably 1–100 parts of tris(hydroxymethyl)aminomethane hydrochloride, most preferably 1–50 parts, are used per part of prostaglandin compound.

The amount of soluble inert filler added will depend on the ultimate use of the prostaglandin compound, but preferably is 0–1000 parts of filler per part of prostaglandin for formulations ultimately intended for enteral administration, 0–200 parts for those formulated for parenteral administration, and 0–1000 parts for those designed for topical application.

The aqueous solutions of prostaglandin compound, etc., are preferably made up with distilled or deionized water, most preferably with sterile double-distilled water.

The solutions of prostaglandin compound and tris(-hydroxymethyl)aminomethane are brought to pH 5–7 by addition of hydrogen chloride in the form of the gas or by solutions of hydrochloric acid, preferably of 0.01–1 normality. The pH of the solution is followed by measurement using a glass electrode.

The solution is then filter sterilized by passing it through a sterilized microporous filter, e.g. Millipore 0.25 micron, and aseptically filled in sterile ampoules, as described in the United States Pharmacopeia (USP. XIX) or in Remington's Pharmaceutical Sciences, 15th Edition 1975, p. 1396–1397 or in The Theory and Practice of Industrial Pharmacy, Lea & Febiger, Philadelphia 1970, p. 163–167.

Lyophilization or freeze-drying of filtered solutions of prostaglandin compound, tris(hydroxymethyl)aminomethane hydrochloride and soluble inert filler is done by techniques as set forth at Remington's Pharmaceutical Sciences, 15th Edition 1975, Mack Publishing Company, Easton, Pennsylvania, p. 1483–1485 or The Theory and Practice of Industrial Pharmacy Lea & Febiger, Philadelphia 1970, p. 45–47.

Prostaglandin-containing lyophilized powders of this invention are stable for longer than a year at 4° C.

The powders of this invention are also stable over a relatively long period at room temperature, on the order of 5 to 10 months.

Prostaglandin $E_2$ freeze-dried from an aqueous-alcoholic solution without addition of tris(hydroxymethyl)aminomethane hydrochloride is decomposed to an extent of more than 30% within three weeks at room temperature.

If buffers, other than tris(hydroxymethyl)aminomethane hydrochloride, customarily used in pharmaceutical formulations, are added to aqueous-alcoholic prostaglandin $E_2$ solutions, rapid decomposition of lyophilized prostaglandin $E_2$ occurs. After addition of sodium citrate/citric acid buffer, pH 3.5, complete decomposition occurs within 12 days after freeze-drying. Addition of triethanolamine/hydrochloric acid buffer, pH 7.0, results in 15% decomposition within one week. With disodium hydrogen phosphate/citric acid buffer, pH 5.6, there is 30% decomposition within two weeks and with addition of disodium hydrogen phosphate/citric acid buffer, pH 5.1, and polyvinylpyrrolidone, there is 10% decomposition of prostaglandin $E_2$ within two weeks at room temperature.

The freeze-dried powder can be processed, using suitable auxiliary agents, into a variety of preparations suitable for enteral, parenteral, or topical application in human or veterinary medicine. Thus, injection or infusion solutions are prepared with physiological NaCl solution. Solid auxiliary agents, for example, mannitol, lactose, corn starch, magnesium stearate, talc, etc., can be used to prepare tablets, powders, capsules, etc.

The invention also relates to the use of the stabilized prostaglandin-containing powders to make formulations for human or veterinary medicine.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Composition of the prostaglandin $E_2$ solution utilized for lyophilization, per ampoule:
1.0 mg. prostaglandin $E_2$
7.5 mg. tris(hydroxymethyl)aminomethane and 5.0 mg. polyvinylpyrrolidone brought to pH 5.0 with 0.1N and 0.01N hydrochloric acid and diluted to a volume of 0.5 ml. with twice-distilled water.

PRODUCTION PROCESS

Prostaglandin $E_2$ is dissolved by addition to an ice-cold solution of polyvinylpyrrolidone and tris(hydroxymethyl)-aminomethane in distilled water. By careful addition of 0.1N and 0.01N hydrochloric acid, the pH of the solution is brought to 5.0 with good cooling. Thereafter, the solution is brought to the required volume. After sterile filtration through a steril membrane filter, the solution is dispensed into sterilized ampoules.

The solution is frozen by dipping the ampoules into an acetone/dry ice freezing mixture and immediately lyophilized in a precooled freeze-drying unit for about 48 hours. After the lyophilization is complete, the ampoules are at once sealed by fusion.

EXAMPLE 2

Composition of prostaglandin solution utilized for lyophilization, per ampoule:
2.0 mg. (5Z, 13E)-(8R,11R,12R,15S)-11,15-dihydroxy-9-oxo-5,13-prostadienoic acid(N-methane-sulfonylamide)
15.0 mg. tris(hydroxymethyl)aminomethane
10.0 mg. polyvinylpyrrolidone, brought to pH 5.0 with 0.1N and 0.01N hydrochloric acid and diluted with twice-distilled water to 1.0 ml.

The procedure described in Example 1 is followed.

EXAMPLE 3

Composition of prostaglandin solution used for lyophilization, per ampoule:
0.05 mg. 16-phenoxy-prostaglandin-$E_2$-methane-sulfonamide
7.50 mg. tris(hydroxymethyl)aminomethane
5.00 mg. polyvinylpyrrolidone, brought to pH 5.0 with 0.1N and 0.01N hydrochloric acid and diluted up to 0.5 ml. with twice-distilled water.

The preparation is treated as set forth in Example 1. The dry preparations are stored in the dark at 4° C.

Lyophilization can also be effected using other suitable containers, for example, multivials.

EXAMPLE 4

Parenteral Solution

A parenteral solution is prepared dissolving the freeze-dried content of one ampoule of Example 1 in 1-100 ml. of sterile physiological NaCl solution under aseptic conditions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can made various changes and modifications of the invention to adapt it to various usages and conditions.

What is claimed is:
1. A storage-stable lyophilized prostaglandin composition comprising a prostaglandin compound and a decomposition-inhibiting quantity of tris (hydroxymethyl) aminomethane acid addition salts, said composition prior to being lyophilized having a pH of about 5-7, and the acid of said acid addition salts being other than said prostaglandin compound.
2. The composition of claim 1, which further contains an inert filler.
3. The composition of claim 1, comprising 1-1000 parts of tris(hydroxymethyl)aminomethane acid addition salts per part of prostaglandin compound.
4. The composition of claim 1, comprising 1-200 parts of tris(hydroxymethyl)aminomethane acid addition salts per part of prostaglandin compound.
5. The composition of claim 1, wherein the acid addition salt is the hydrochloride.
6. The composition of claim 3, which further contains up to 1000 parts of inert filler per part of prostaglandin compound.
7. The composition of claim 3, which further contains 1-200 parts of inert filler per part of prostaglandin compound.
8. The composition of claim 2, wherein the inert filler is polyvinylpyrrolidone.
9. The composition of claim 1, wherein the prostaglandin compound is a prostaglandin $E_2$ compound.
10. The composition of claim 1, wherein the prostaglandin compound is (5Z,13E)-(8R,11R,12R,15S)-11,15-dihydroxy-9-oxo-5,13-prostadienoic acid-(N-methanesulfonylamide).
11. The composition of claim 1, wherein the prostaglandin compound is 16-phenoxyprostaglandin-$E_2$-methanesulfonamide.
12. A process for preparing the storage-stable, lyophilized composition of claim 1, comprising dissolving a prostaglandin compound and tris(hydroxymethyl)aminomethane in a solvent, bringing the pH of the solution to 5-7 by introduction of an acid other than said prostaglandin compound, filtering said solution, and lyophilizing the filtrate from said solution.
13. The process of claim 12, wherein the solvent is water or a mixture of water and a water-miscible, highlyvolatile solvent.
14. The process of claim 12, wherein a filler is dissolved in said solution.
15. The process of claim 12, wherein the filler is polyvinylpyrrolidone.
16. The process of claim 12, wherein the acid is hydrogen chloride.
17. An aqueous solution of a prostaglandin compound and a decomposition-inhibiting quantity of an acid addition salt of tris(hydroxymethyl)aminomethane, said solution having a pH of about 5-7, the acid of said acid salt being other than said prostaglandin.
18. An aqueous solution according to claim 17, said prostaglandin being a prostaglandin $E_2$ compound.
19. A solution according to claim 18 wherein said acid addition salt is a hydrochloride.

* * * * *